United States Patent [19]

Giesy et al.

[11] Patent Number: 4,824,435
[45] Date of Patent: Apr. 25, 1989

[54] INSTRUMENT GUIDANCE SYSTEM

[75] Inventors: Jerry D. Giesy, Portland; Matthew W. Hoskins, Beaverton, both of Oreg.

[73] Assignee: Thomas J. Fogarty, Palo Alto, Calif.

[21] Appl. No.: 51,864

[22] Filed: May 18, 1987

[51] Int. Cl.⁴ .............................................. A61M 31/00
[52] U.S. Cl. .................................. 604/49; 128/303 R; 128/348.1; 128/772; 128/328; 604/280; 604/52; 604/54
[58] Field of Search ................... 128/303 R, 328, 344, 128/348.1, 657, 772; 604/96–103, 280, 356, 93, 49, 52, 54

[56] References Cited

U.S. PATENT DOCUMENTS

| | | | |
|---|---|---|---|
| 2,657,691 | 11/1953 | Nordstrom, Jr. | 128/303 R |
| 2,936,760 | 5/1960 | Gants | 604/102 |
| 3,225,762 | 12/1965 | Guttman | 604/164 |
| 3,766,924 | 10/1973 | Pidgeon | 128/344 |
| 4,236,521 | 12/1980 | Lauterjung | 604/270 |
| 4,545,390 | 10/1985 | Leary | 128/772 |

FOREIGN PATENT DOCUMENTS

| | | | |
|---|---|---|---|
| 2934628 | 3/1981 | Fed. Rep. of Germany | 604/270 |
| 8603129 | 6/1986 | Fed. Rep. of Germany | 604/96 |
| 0591963 | 7/1925 | France | 604/270 |

Primary Examiner—Dalton L. Truluck
Assistant Examiner—Denise Whelton
Attorney, Agent, or Firm—Limbach, Limbach & Sutton

[57] ABSTRACT

Elongate flexible elements are guided into place within a tortuous body passage by providing the elements with annular guides adjacent their distal ends and sliding the elements over a guide wire extended through the passage. Column strength to move the elements through the body passage may be provided by a tubular pusher slidably received on the guide wire. The annular guides are localized at the distal ends of the members so that a plurality of members may be sequentially or simultaneously guided into place over a single guide wire.

6 Claims, 3 Drawing Sheets

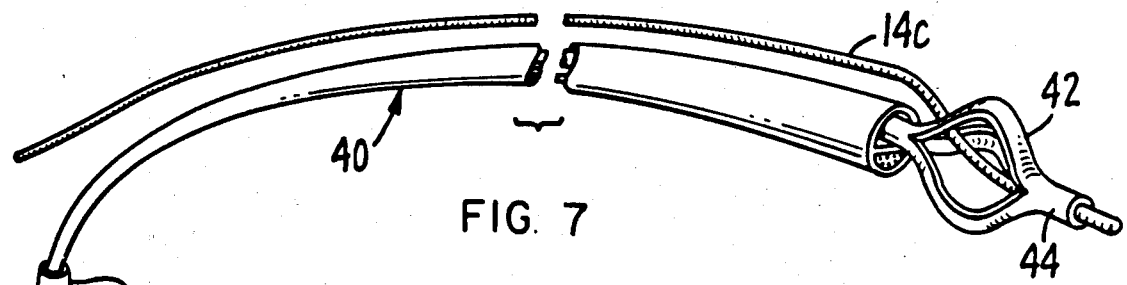
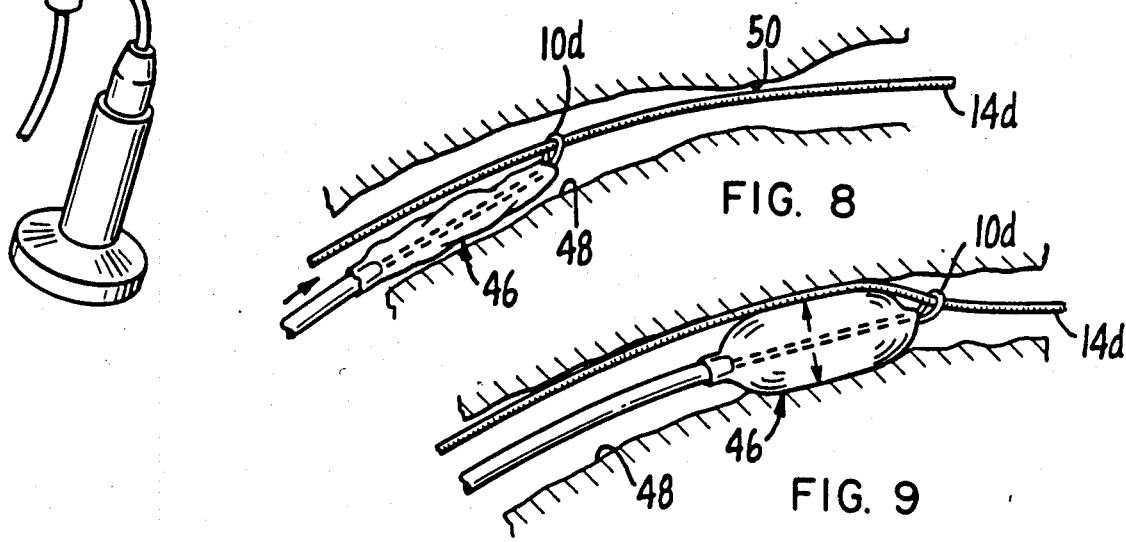
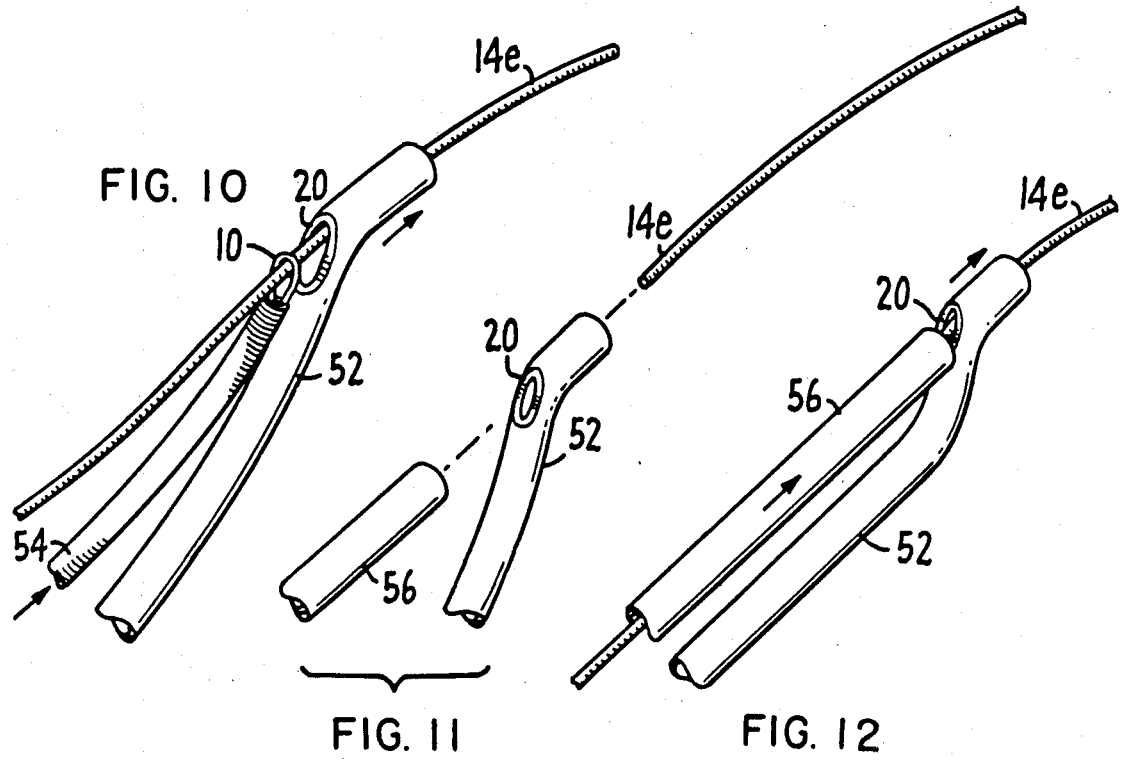

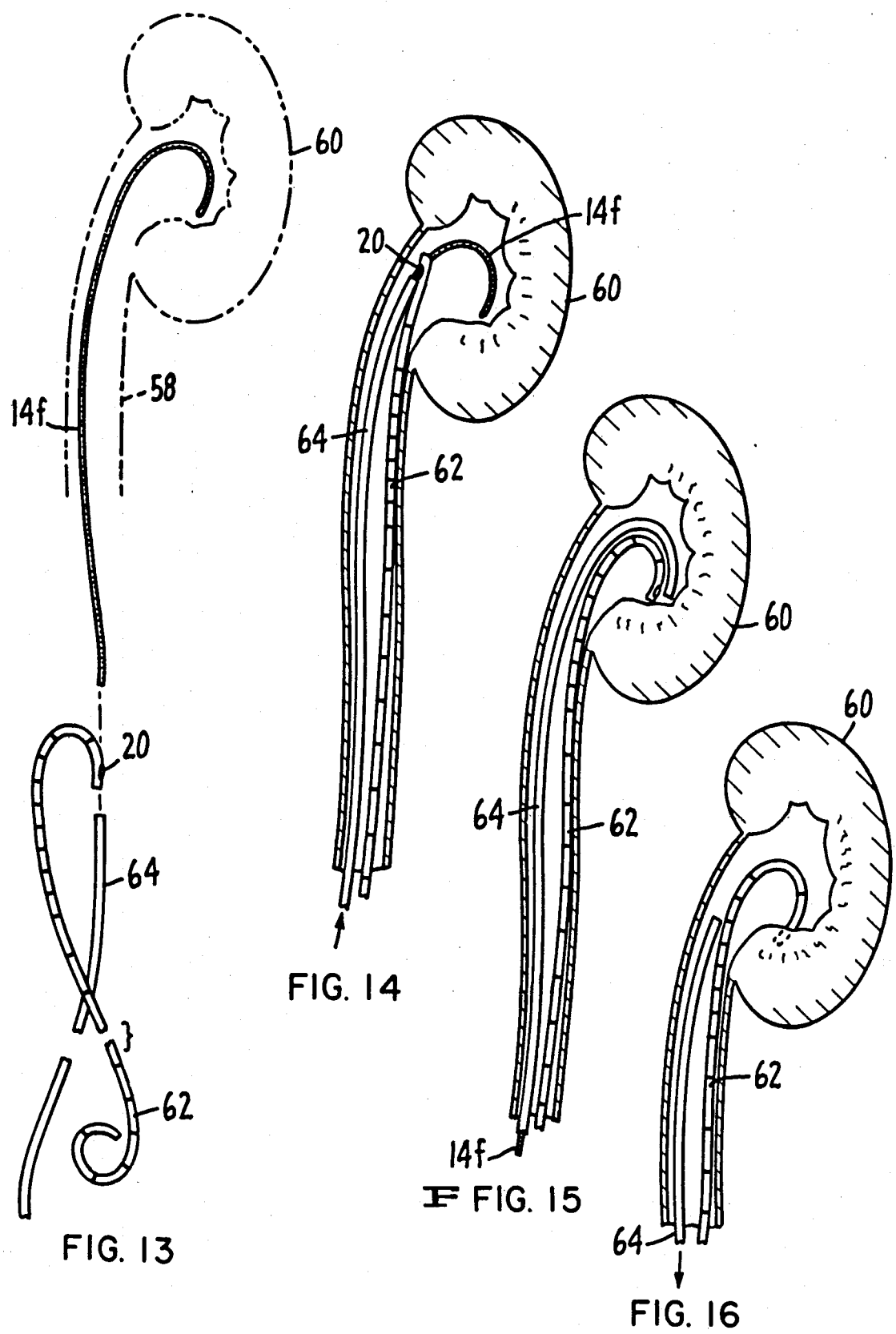

INSTRUMENT GUIDANCE SYSTEM

BACKGROUND OF THE INVENTION

The present invention relates to a method and apparatus for guiding diagnostic and therapeutic devices into tortuous body passages, such as may be found in the urologic, cardiovascular, gastrointestinal and pulmonary systems. In its more specific aspects, the invention is concerned with a system which employs a guide wire to guide the instrument into place and an improved guide for traversal over the wire to direct an instrument to the desired location.

In the prior art, it has been common to place instruments within body passages by passing the instruments over a previously placed guide wire. This technique ensures that the instrument will follow the correct pathway and helps minimize trauma associated with instrument advancement. Guidance is normally accomplished by threading the previously placed guide wire through a lumen which runs the entire length of the instrument. This lumen, typically called a "through-lumen", can serve other functions besides guide wire accommodation, such as: fluid infusion, pressure monitoring, or the passage of other instruments for visualization and therapy.

An example of a prior art system where an instrument is advanced over a previously placed guide wire may be seen in U.S. Pat. No. 4,526,175. In the device of that patent, a through-lumen runs the full length of the instrument to accommodate a guide wire. It is also known in the prior art to provide an instrument carrier wherein a preformed catheter is placed in advance of the instrument, much as a guide wire would be placed, and then the instrument is passed through the catheter to position the instrument within a body passage. Such a system may be seen in U.S. Pat. No. 4,195,637.

SUMMARY OF THE INVENTION

In its broadest aspects, the invention is concerned with a system for guiding instruments into tortuous body passages through means of a guide which is secured externally of the instrument and is adapted to be threaded along a prepositioned guide wire. In the preferred embodiment, the guide comprises an angular member which may be threaded over the guide wire and allows passage of an instrument over the wire without the use of a through-lumen. In the preferred arrangement, the guide is positioned at the tip or distal end of the instrument. The instrument is advanced alongside the guide wire and is kept on course via the guide at the instrument.

A principle object of the invention is to provide a guide system whereby an instrument may be passed into place via a guide wire, without the need of a through-lumen within the instrument.

Another object related to the latter object is to provide a guide system which is of a bulk lower than that of conventional through-lumen systems.

A further object of the invention is to provide a guide system for directing instruments into body passages over a prepositioned guide wire wherein multiple instruments may be simultaneously or individually directed into place over the wire.

Still another object of the invention is to provide a system wherein a guide wire of a preformed curvature may be placed within a body passage, and an instrument may be advanced over the wire to follow its curvature.

Another object of the invention is to provide a system wherein instruments of low column strength may be advanced into place over a guide wire by a pusher which functions, in association with a guide engaged with the wire, to draw the instrument along the wire.

The further object of the invention is to provide a guide system wherein a variety of instruments may be passed into place over a guide wire, without materially altering the construction of the instruments or requiring that they be provided with through-lumens.

These and other objects will become more apparent when viewed in light of the following description and accompanying drawings.

BRIEF DESCRIPTION OF THE DRAWINGS

FIG. 7 is a perspective view of an obturator and optical scope device being advanced over a guide wire passing through a modified form of the tubular tip embodiment of the invention;

FIG. 8 is a cross-sectional view of the loop tip embodiment of the invention being used to guide a balloon catheter into treating relationship with a constricted body passage;

FIG. 9 is a cross-sectional view similar to FIG. 8, illustrating the balloon in treating relationship with the constricted passage and inflated to dilate the passage;

FIG. 10 is a perspective view illustrating a tubular catheter an a secondary guide wire being simultaneously guided into place over a primary guide wire;

FIG. 11 is an exploded perspective view illustrating how a catheter embodying the tubular tip embodiment of the invention would be applied to a guide wire with a pusher which may be employed to force the catheter along the wire;

FIG. 12 is a view similar to FIG. 11, illustrating the catheter and pusher in place on the guide wire;

FIG. 13 is an exploded view illustrating a kidney and associated ureter in phantom, with a preformed curvalinear guide wire extending through the ureter and into the kidney and an elastomeric stent positioned for guidance over the wire through means of the loop tip embodiment of the invention; and, FIGS. 14, 15, and 16 are cross-sectional views of the kidney and ureter of FIG. 13, sequentially illustrating the loop tip embodiment being used to direct the stent into the kidney with a pusher threaded over the wire.

DESCRIPTION OF THE PREFERRED EMBODIMENTS

Figure 1:
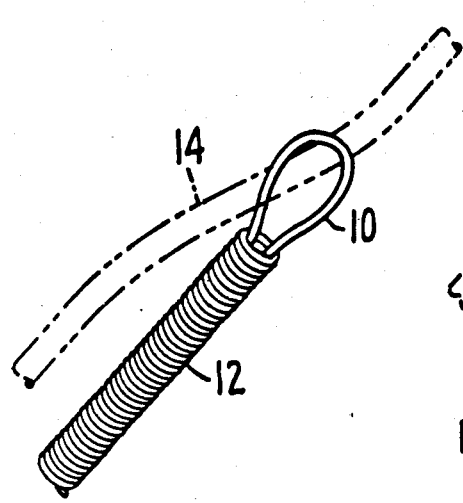
FIG. 1 is a fragmentary perspective view of a loop guide embodiment of the invention secured to the distal end or tip of an instrument which takes the form of a secondary guide wire, with the primary guide wire over which the instrument is being threaded shown in phantom.
Figure 3:
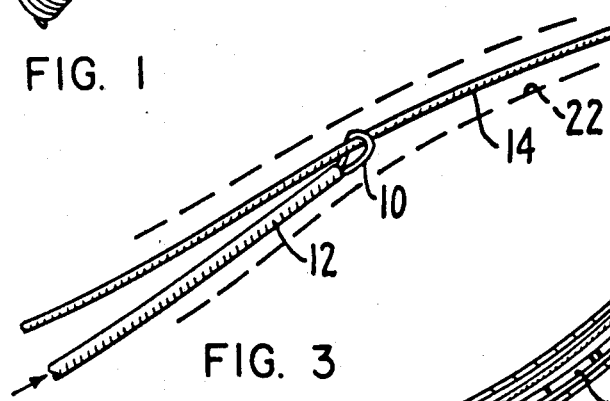
FIG. 3 is a perspective view of the loop guide embodiment of the invention in the process of being moved through a body passage shown in phantom lines, illustrating the manner in which the secondary guide wire instrument is advanced along side the primary guide wire.

The loop guide embodiment of the invention illustrated in FIGS. 1 and 3 comprises a loop 10 secured to the tip or distal end of the instrument to be placed. As exemplified in FIGS. 1 and 3, the instrument comprises a secondary guide wire 12; the primary guide wire over which the instrument is being directed is designated by the numeral 14. The loop may be formed as a wire or plastic element. The only requirement being that it have an internal diameter sufficient to freely slide over the primary guide wire. The primary guide wire may have any suitable cross-section, for example 2 to 6 French.

Figure 2:
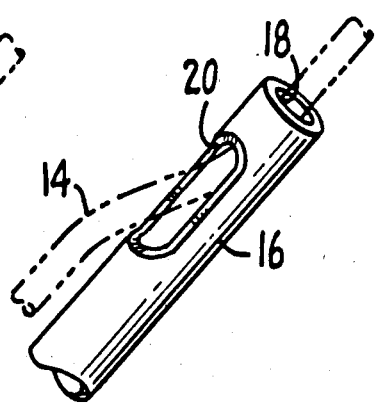
FIG. 2 is a fragmentary perspective view of a tubular tip embodiment of the invention being threaded over a guide wire shown in phantom.

The tubular tip embodiment of the invention shown in FIG. 2 comprises the tube 16 having an opening 18 in its distal end and a lateral cut out or opening 20 in its side adjacent to distal end. The openings are connected by the lumen of the tube and, together, define an annular opening through which a primary guide wire 14, as shown in phantom in FIG. 2, may be passed.

FIG. 3 shows the loop guide embodiment directing the secondary guide wire 12 over a primary guide wire 14 extending through a body passage 22. In this illustration, the secondary guide wire 12 has a column strength sufficient to enable it to be pushed along the primary guide wire, without any secondary stiffening or pushing means.

Figure 4:
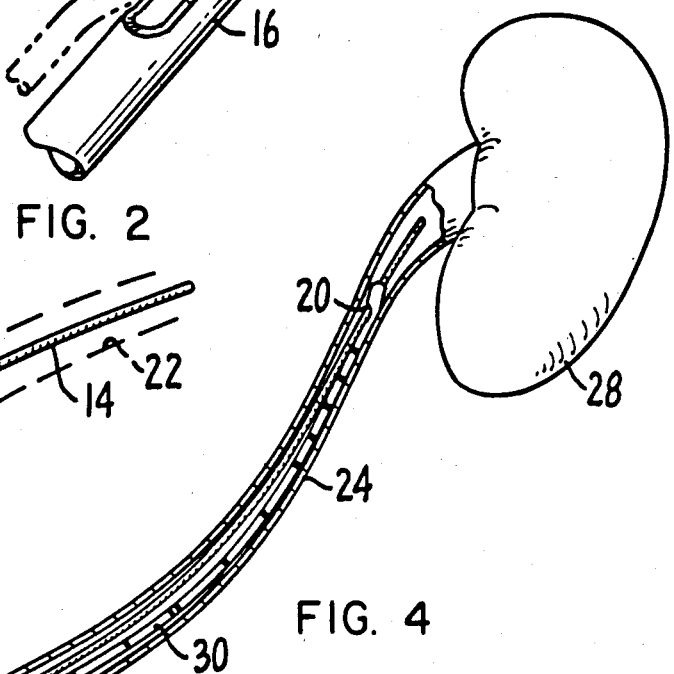
FIG. 4 is a diagrammatic perspective view, with parts thereof broken away, illustrating the tubular tip embodiment of the invention being used to advance a catheter over a guide wire located in the ureter of the urologic system.

In FIG. 4, the body passage being traversed is a ureter 24 extending from bladder 26 to kidney 28. A primary guide wire 14a extends from the bladder in through the ureter. The catheter being directed into place over the guide wire is designated by the numeral 30. At its distal end, the catheter is formed with open distal and lateral openings which are connected through the catheter body to provide a guide of the tubular tip type shown in FIG. 2. This guide is threaded over the guide wire 14a. The catheter is of sufficient column strength to enable it to be pushed along the guide wire without the aid of a pusher or stiffener element.

Figure 5:
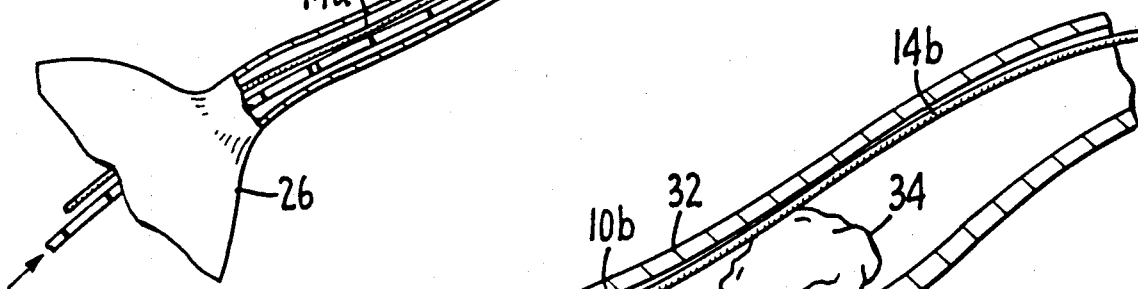
FIG. 5 is a cross-sectional view of a ureter having a stone lodged therein, with the loop guide embodiment of the invention in the process of being used to advance a stone basket toward the stone.
Figure 6:
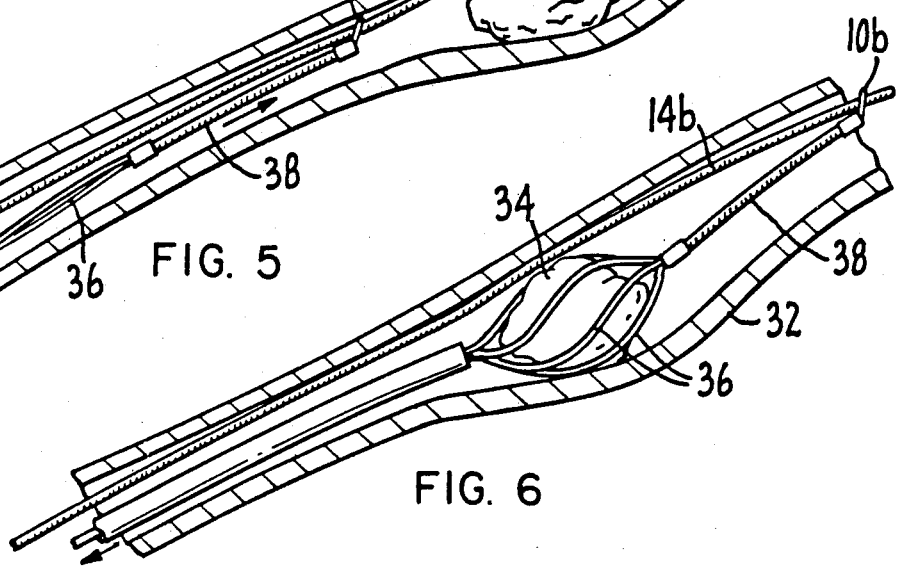
FIG. 6 is a cross-sectional view similar to FIG. 5, illustrating the stone basket after it has been advanced into place and captured the stone.

The ureter shown in FIGS. 5 and 6 is designated by the numeral 32 and is shown having a stone 34 lodged therein. A guide wire 14b is shown as having been extended through the ureter 32 and past the stone 34. A stone basket, designated 36, is guided along the wire 14b by a loop 10b secured to a wire extension 38 on the basket.

As shown in FIGS. 5 and 6, the stone basket assembly has a column strength sufficient to enable it to be directed along the guide wire 14b without the aid of a stiffener or pusher element. During initial placement, the basket is maintained in a collapsed condition as shown in FIG. 5 until is passed by the stone 34. Thereafter, the basket is expanded and withdrawn to capture the stone and remove it from the ureter. The captured condition is shown in FIG. 6. There it will also be seen that the guide loop 10b remains in slidable engagement with the wire 14b as the basket is withdrawn from the ureter. Such engagement of the loop 10b with the guide wire during withdrawal aids in assuring that the basket will be withdrawn along side the guide wire.

The scope and obturator instrument of FIG. 7 is designated in its entirety by the numeral 40 and is shown in the process of being directed over a guide wire 14c. The obturator portion of the instrument is designated by the numeral 42 and is shown as having a tubular extension 44 at its distal end through which the wire 14 slidably extends. Thus, the instrument may be threaded into place over the guide wire, similarly to the manner in which the catheter shown in FIG. 4 is directed in to place.

The balloon catheter shown in FIGS. 8 and 9 is designated in its entirety by the numeral 46 and is shown as having a loop guide 10d secured to its distal end and threaded over a guide wire 14d. The body passage shown in FIGS. 8 and 9 is designated by the numeral 48 and is shown as having a partially restricted occluded area 50 formed therein.

In practice, the guide wire 14d is first extended through the body passage 48 and past the occluded area 50 to be treated. Then the balloon catheter 46 is threaded over the guide wire through means of the loop guide 10d until the balloon portion of the catheter is disposed within the occluded area. Thereafter, the balloon is inflated to dilate the area. As with the earlier described embodiments, the balloon catheter assembly has a column strength sufficient to enable it to be directed into place over the guide wire 14d, without the aid of pushers or stiffening elements.

The guide wire shown in FIG. 10 is designated by the numeral 14e and is shown in the process of having a catheter 52 and secondary guide wire 54 simultaneously moved therealong. The catheter 52 has tip conformed as the tubular tip embodiment of the guide shown in FIG. 2. The wire 54 has a guide loop corresponding to that of the FIG. 1 embodiment. The secondary guide wire 54 has sufficient column strength to enable it to be moved along the guide wire 14a and to push the catheter 52, without the aid of separate stiffener of pusher elements.

FIGS. 11 and 12 illustrate the catheter 52 being applied to and directed along the guide wire 14e with the aid of a tubular pusher 56 threaded over the guide wire. The pusher 56 provides column strength and enables the catheter 52 to be slid over the wire 14a, even though the catheter is not of sufficient column strength to enable it to be pushed into place from its proximal end.

FIGS. 13 to 16 show a primary guide wire 14f of a preformed curvalinear configuration extended through a ureter 58 and into the body of a kidney 60. The purpose of the curvalinear guide wire is to enable an elastomeric stent to be guided into engaged condition within the kidney. The stent, as may be seen in FIG. 14 is formed with precurved ends, one of which is designed to snap into engaged condition within the kidney cavity and the other of which is designed to snap into engaged condition within the bladder (not illustrated).

It should be appreciated that the elastomeric stent is of very low column strength. Thus, it is not capable of sustaining itself so that it may be pushed into place from its proximal end. As shown, the distal end of the stent is provided with a tubular tip similar to that shown in FIG. 2. This tip is threaded over the guide wire 14f and then a tubular pusher 64 is threaded over the guide wire and into engagement with the tip. The pusher serves to draw the stent along the guide wire, as may be seen from the sequence of FIGS. 14 and 15. Ultimately, the pusher pushes the tubular guide tip off the end of the guide wire 14f, as may be seen in FIG. 16. Thereafter, the guide wire and stent may be removed, as illustrated in FIG. 16, leaving the stent engaged within the kidney.

CONCLUSION

While preferred embodiments of the invention have been illustrated and described, it should be understood that the invention is not intended to be limited to these embodiments, but rather is defined by the accompanying claims.

We claim:

1. An improved method of positioning a member within a tortuous body passage, said method comprising: extending a guide wire into the passage to the location where it is desired to position the member; providing a narrow annular loop external of the member and secured thereto solely adjacent the distal end of the member; threading the annular loop over the guide wire whereby the loop may follow the wire while permitting hinged articulation of the member relative to an away from the wire at the point of connection of the loop to the wire; and, sliding the annular loop along the guide wire to direct the member to the desired position within the body passage.

2. An improved method of positioning first and second members within a tortuous body passage, said method comprising: extending a guide wire into the passage to the locations where it is desired to position the members; providing each of said members with a narrow annular loop external of the member and secured thereto solely adjacent the distal end thereof; threading the loops over the guide wire whereby the loops may follow the wire while permitting articulation of the respective members relative to an away from the wire; sliding the loops along the guide wire to direct the members to the desired positions within the body passage.

3. A method according to claim 2 wherein the members are of an elongate flexible configuration.

4. An improved method of positioning a member within a tortuous body passage, said method comprising: extending a guide wire into the passage to the location where it is desired to position the member; extending a short tubular segment from the distal end of the member, said segment, together with closely spaced openings in the side and the distal end thereof, providing a narrow annular loop secured to the member; threading the annular loop over the guide wire whereby the loop may follow the wire while permitting articulation of the member relative to and away from the wire; and, sliding the annular loop along the guide wire to direct the member to the desired position within the body passage.

5. A method according to claim 4 wherein the loop is slid along the wire by sliding the pusher element over the wire and into engagement with the loop to move the loop along the wire.

6. A method according to claim 5 wherein the pusher element comprises a tubular element having a passage therein slidably received on the wire.

* * * * *

UNITED STATES PATENT AND TRADEMARK OFFICE
CERTIFICATE OF CORRECTION

PATENT NO. : 4,824,435
DATED : April 25, 1989
INVENTOR(S) : Jerry D. Giesy et al It is certified that error appears in the above-identified patent and that said Letters Patent is hereby corrected as shown below:

On the title page inventors should read

--Jerry D. Giesy, Portland; Matthew W. Hoskins, Beaverton, both of Oreg., George D. Hermann, Palo Alto, California--.

Signed and Sealed this

Thirteenth Day of March, 1990

Attest:

JEFFREY M. SAMUELS

*Attesting Officer*   Acting Commissioner of Patents and Trademarks